United States Patent [19]

Hoefer

[11] Patent Number: 4,560,459
[45] Date of Patent: Dec. 24, 1985

[54] VERTICAL GEL SANDWICH FOR USE IN ELECTROPHORESIS AND METHOD THEREFOR

[75] Inventor: Peter S. Hoefer, San Francisco, Calif.

[73] Assignee: Hoefer Scientific Instruments, San Francisco, Calif.

[21] Appl. No.: 581,695

[22] Filed: Feb. 21, 1984

[51] Int. Cl.[4] ............................................. G01N 27/28
[52] U.S. Cl. .............................. 204/182.8; 204/299 R; 249/160; 249/163; 249/164; 249/168; 249/169
[58] Field of Search ....................... 204/299 R, 180 G; 249/160, 163, 164, 168, 169

[56] References Cited

U.S. PATENT DOCUMENTS

| | | | |
|---|---|---|---|
| 3,881,683 | 5/1975 | Whitney | 249/163 |
| 4,035,377 | 7/1977 | Detroy | 204/180 G |
| 4,279,401 | 7/1981 | Ramirez et al. | 249/169 |
| 4,325,796 | 4/1982 | Hoefer et al. | 204/299 R |

*Primary Examiner*—Andrew H. Metz
*Assistant Examiner*—B. J. Boggs, Jr.
*Attorney, Agent, or Firm*—Flehr, Hohbach, Test, Albritton & Herbert

[57] ABSTRACT

A vertical gel sandwich for use in electrophoresis and a method of assembling is provided by the use of a pair of T-shaped spacers between the two plates of a gel sandwich. The stem of the T spaces the plates apart to form the gel slot and the head of the T being flush with the sides of both plates provides for alignment of the spacers and also prevents shifting.

5 Claims, 9 Drawing Figures

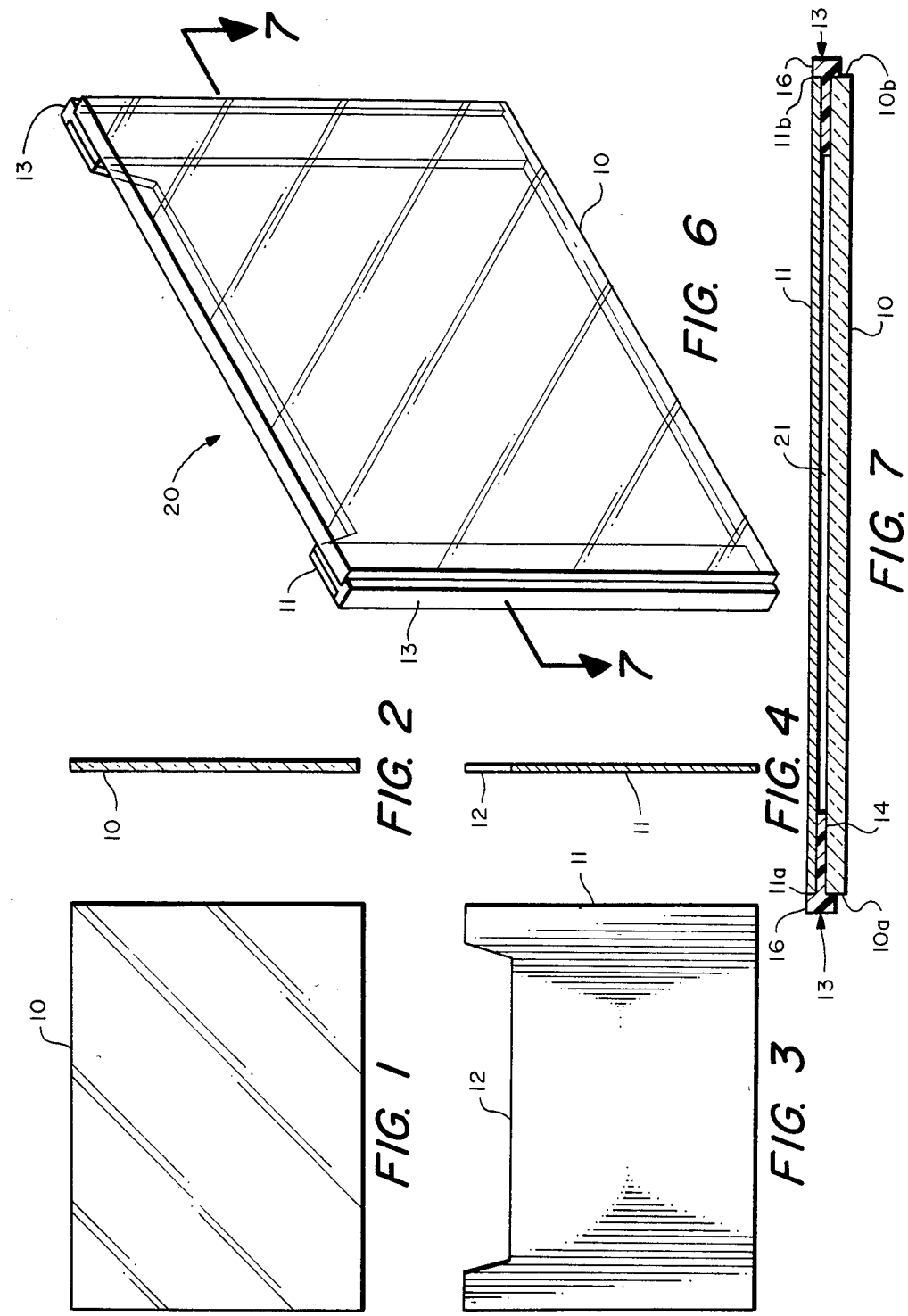

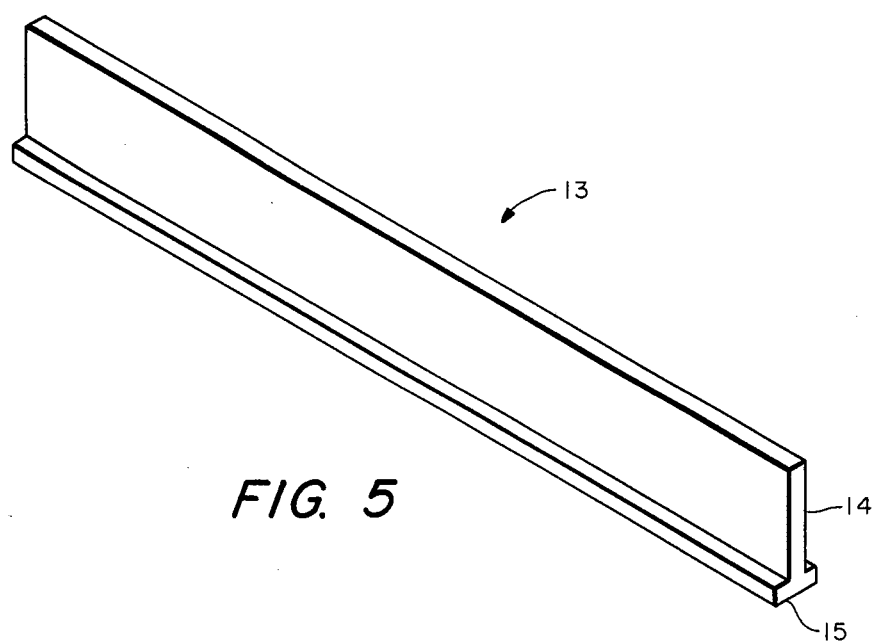
FIG. 5
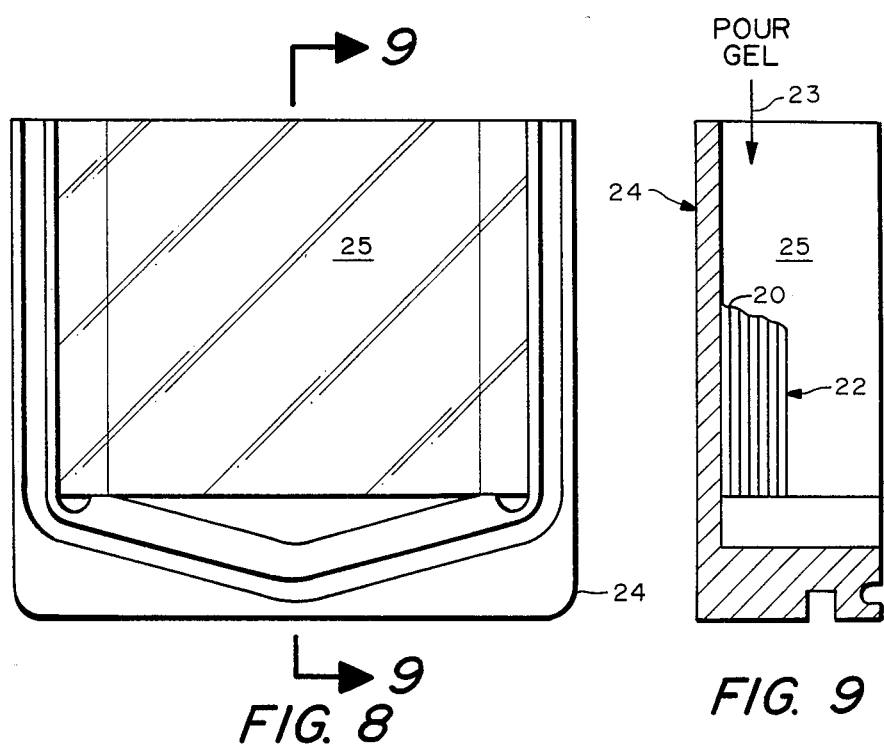
FIG. 8
FIG. 9

VERTICAL GEL SANDWICH FOR USE IN ELECTROPHORESIS AND METHOD THEREFOR

The present invention is directed to a vertical gel sandwich for use in electrophoresis and a method therefor.

When carrying out the process of gel electrophoresis, it is necessary to first construct a sample unit filled with gel and secondly apply an appropriate voltage to cause electrophoretic separation of the sample within the gel slab. A sample unit normally consists of a pair of, for example, glass plates, with a pair of spacers in the form of thin strips to separate the plates and form a slot in which a gel is later poured. This is also termed a gel sandwich.

A typical sample unit is shown in U.S. Pat. No. 4,325,796 which is assigned to the present assignee. While the foregoing technique using flat spacers is suitable for larger size sample units or gel sandwiches, the process of assembling the sandwich may still be awkward for some users and particularly so when smaller mini-type gel sandwiches are desired.

Thus, it is a general object of the present invention to provide an improved vertical gel sandwich for use in electrophoresis and method therefor.

In accordance with the above object, there is provided a vertical gel sandwich for use in electrophoresis comprising a pair of juxtaposed plates. Means are provided for spacing the plates apart to form a gel slot including a pair of T-shaped spacers, the stem of the T being inserted between the plates and providing a pair of side boundaries for the gel slot. The head of the T fits flush against the sides of the pair of plates to thereby align its stem portion parallel to the sides and to prevent shifting of the spacer.

There is also provided a method of assembling a sandwich for use in electrophoresis. It comprises the steps of laying down one plate of a pair and placing a pair of elongated T-shaped spacers on opposite sides of the plates with the head of the T flush against the side of the plate. The other plate of the pair is placed on the spacers with the sides of such plate being against the respective heads of the T-spacers whereby a sandwich is formed with a slot. The slot is then filled with gel.

FIG. 1 is a front elevational view of one of the plates of a sandwich.

FIG. 2 is a cross-sectional view of FIG. 1.

FIG. 3 is a front elevational view of the other of the plates of a sandwich.

FIG. 4 is a cross-sectional view of FIG. 3.

FIG. 5 is a perspective view of a T-shaped spacer used in the present invention.

FIG. 6 is a perspective view of the gel sandwich embodying the present invention.

FIG. 7 is an enlarged cross-sectional view taken along line 7—7 of FIG. 6 showing the method of assembling the sandwich of the present invention.

FIG. 8 is a front elevational view of a casting container used in the present invention.

FIG. 9 is a cross-sectional view taken along line 9—9 of FIG. 8 and also showing a plurality of the sandwiches of FIG. 6 as they would be placed in the casting container.

The gel sandwich of the present invention is formed by a rectangular glass plate 10 as one side of the sandwich as illustrated in FIGS. 1 and 2 and an alumina plate 11 as illustrated in FIGS. 3 and 4. The alumina plate 11 includes an upper notch 12 which is utilized to expose the gel in the sandwich to an upper buffer solution and thus an applied voltage for the purpose of electrophoresis. Plates 10 and 11 except for the notch 12 have identical dimensions which, for example, would be 10 centimeters wide and 8 centimeters high.

Alternatively, the two plates could both be constructed of glass with the second plate notched or not.

FIG. 5 illustrates one of two T-shaped spacers 13 which are used to space and separate the plates. The T-shaped spacer 13 has a stem portion 14 and a head portion 16.

Referring to FIGS. 6 and 7, there is illustrated an assembled gel sandwich 20.

The following are the steps used in assembling a single sandwich. First, the glass plate 10 is laid on a flat surface or placed in the palm of a hand. Next, a pair of spacers 13 are placed on opposite sides of plate 10 with the head 16 of the T being flush or abutting against the sides 10a and 10b of plate 10. Then the other plate 11 is placed on the spacers with the sides 11a and 11b also flush against the head 16 of the T-spacer 13. Thus, a first sandwich has been formed. And in the middle of the sandwich is an unoccupied space or gel slot 21 into which is later poured a gel for use in electrophoresis.

The T-shaped spacers 13, as illustrated in FIGS. 6 and 7, thus provide a pair of side boundaries for the gel slot 21. Also the head 16 of the T by fitting flush against the sides of the pair of plates 10 and 11 thereby aligns the stem portion 14 so that it is parallel to the sides of the plates. Finally, the above construction prevents shifting of the spacers when the sandwich is moved.

When the foregoing is done, in one typical mode of operation, immediately upon formation or completion of the first sandwich 20, as illustrated in FIGS. 6 and 7, it is vertically stacked in the gel casting container 24 of FIGS. 8 and 9. This container retains several of the sandwiches in a vertical orientation in a U-shaped cutout 25 as illustrated in FIG. 9, and designated as a cassette 22. While in this orientation, gel is poured into the various gel slots 21 as indicated by the "pour gel" arrow indication 23. Then they are wrapped and stored in a refrigerator and used one at a time as needed.

Alternatively, gel may be cast or poured into the slot 21 of a sandwich or sample unit when it is mounted on the electrophoresis unit.

In actual use, a single sandwich 20 is clamped onto a vertical slab gel electrophoresis unit such as, for example, the model SE200 manufactured and sold by the assignee of the present invention. The sample unit or gel sandwich is clamped onto the electrophoresis unit in such a manner that the notch 12 in the plate 11 contacts an upper buffer solution, the bottom of the slot 21 makes contact with a lower buffer solution, and then when a voltage is applied between the two buffer solutions electrophoretic action will take place.

From another aspect, the present invention offers a technique of conveniently forming cassettes that can be distributed on the market as precast gels to provide increased convenience.

In summary, the T-shaped spacers provide for automatic self-alignment in building a gel sandwich and makes any subsequent handling much easier.

What is claimed:

1. A method of assembling a gel sandwich for use in electrophoresis comprising the following steps:
   laying down one plate of a pair;

placing a pair of elongated straight T-shaped spacers with stems having planar parallel faces on opposite sides of said plate with the head of each T spacer flush against the side of the plate and the face of the stem of said T spacer being contiguous with said plate;

placing the other plate of said pair on said spacers with the sides of such plate flush against the respective heads of said T spacers and with the faces of the respective stems contiguous to the plates whereby a sandwich is formed and having a slot and the top and bottom of said gel slot remain open to allow application of a voltage to a gel in said slot for electrophoretic separation; and pouring gel into said slot in said sandwich.

2. A method as in claim 1 where a casting container is provided including the step of vertically orienting a plurality of said sandwiches in said container for facilitating said gel pouring.

3. A vertical gel sandwich for use in electrophoresis comprising:

a pair of juxtaposed flat plates with gel therebetween;

means for spacing said plates apart and parallel with each other to form a gel slot including a pair of straight T-shaped spacers, the stem of the T having planar parallel faces and being inserted between said plates providing a pair of side boundaries for said gel slot and the top and bottom of said gel slot remain open to allow application of a voltage to said gel for elecrtrophoretic separation, the head of the T fitting flush against the sided of said pair of plates and the parallel faces of the stem of said T spacer being contiguous with said plates to thereby align its stem portion parallel to said sides of such plates and to prevent shifting of said spacer.

4. A gel sandiwch as in claim 3 where said sides of said plates have a minimum predetermined thickness said head of said T-spacer having a corresponding dimension no greater than said thickness.

5. A gel sandwich as in claim 3 togetehr with a casting container for retaining a plurality of said sandwiches in a vertical orientation to allow the pouring of gel into said gel slots.

* * * * *